US012773119B2

(12) United States Patent
Zhao

(10) Patent No.: US 12,773,119 B2
(45) Date of Patent: Oct. 27, 2026

(54) WEARABLE DEVICE, AND HEART RATE TRACKING METHOD AND APPARATUS THEREOF

(71) Applicant: Anhui Huami Health Technology Co., Ltd., Hefei (CN)

(72) Inventor: Mingxi Zhao, Hefei (CN)

(73) Assignee: Anhui Huami Health Technology Co., Ltd., Hefei (CN)

( * ) Notice: Subject to any disclaimer, the term of this patent is extended or adjusted under 35 U.S.C. 154(b) by 869 days.

(21) Appl. No.: 17/868,488

(22) Filed: Jul. 19, 2022

(65) Prior Publication Data

US 2022/0354377 A1 Nov. 10, 2022

Related U.S. Application Data

(63) Continuation of application No. PCT/CN2022/078681, filed on Mar. 1, 2022.

(30) Foreign Application Priority Data

Apr. 26, 2021 (CN) ......................... 202110455923.6

(51) Int. Cl.
*A61B 5/024* (2006.01)
*A61B 5/00* (2006.01)

(52) U.S. Cl.
CPC ...... *A61B 5/02438* (2013.01); *A61B 5/02416* (2013.01); *A61B 5/721* (2013.01);
(Continued)

(58) Field of Classification Search
CPC ............ A61B 5/02438; A61B 5/02416; A61B 5/7257; A61B 5/7264; A61B 2562/0219; A61B 5/7203; A61B 5/7282; A61B 5/72
See application file for complete search history.

(56) References Cited

U.S. PATENT DOCUMENTS

2004/0260540 A1 12/2004 Zhang
2008/0045844 A1* 2/2008 Arbel .................. A61B 5/4035 600/484

(Continued)

FOREIGN PATENT DOCUMENTS

CN 105105737 A 12/2015
CN 106798552 A 6/2017

(Continued)

OTHER PUBLICATIONS

Extended European Search Report for European Application No. 22710946.9 dated Sep. 19, 2023.

(Continued)

*Primary Examiner* — Adam J Eiseman
*Assistant Examiner* — Lucy Eppert
(74) *Attorney, Agent, or Firm* — Young Basile Hanlon & MacFarlane, P.C.

(57) ABSTRACT

Provided are a wearable device, as well as a heart rate tracking method and a heart rate tracking apparatus thereof. The method includes obtaining a photo pethysmo graphic (PPG) signal of the wearable device within a preset time, obtaining a frequency spectrum corresponding to the PPG signal by a short-time Fourier transformation of the PPG signal, generating a curve cluster according to the frequency spectrum, and in response to determining a curve that meets a preset condition in the curve cluster, acquiring a jumped heart rate according to the curve that meets the preset condition to track the heart rate.

20 Claims, 5 Drawing Sheets

(52) U.S. Cl.
CPC .......... *A61B 5/7257* (2013.01); *A61B 5/7264* (2013.01); *A61B 2562/0219* (2013.01)

(56) References Cited

U.S. PATENT DOCUMENTS

| | | | | |
|---|---|---|---|---|
| 2015/0190062 | A1* | 7/2015 | Han | A61B 5/11 600/479 |
| 2015/0313549 | A1* | 11/2015 | Lee | A61B 5/7214 600/479 |
| 2016/0249820 | A1 | 9/2016 | Puig et al. | |
| 2017/0020398 | A1* | 1/2017 | Emadzadeh | A61B 5/02438 |
| 2017/0071489 | A1* | 3/2017 | Presura | A61B 5/681 |
| 2018/0110469 | A1 | 4/2018 | Maani et al. | |
| 2018/0296106 | A1* | 10/2018 | Gu | A61B 5/7257 |
| 2019/0192018 | A1* | 6/2019 | Zhang | A61B 5/02416 |
| 2019/0380592 | A1* | 12/2019 | Priyankara | A61B 5/7203 |

FOREIGN PATENT DOCUMENTS

| | | |
|---|---|---|
| CN | 108478206 A | 9/2018 |
| CN | 110169764 A | 8/2019 |

OTHER PUBLICATIONS

Murthy et al.; Multiple Spectral Peak Tracking for Heart Rate Mointoring from Photoplethysmography Signal During Intensive Physical Exercise; IEEE Signal Processing Letters; Dec. 31, 2015; pp. 2391-2393.

International Search Report and English Translation for International Application No. PCT/CN2022/078681 dated Apr. 19, 2022.

* cited by examiner

WEARABLE DEVICE, AND HEART RATE TRACKING METHOD AND APPARATUS THEREOF

CROSS-REFERENCE TO RELATED APPLICATION(S)

The present application disclosure is a continuation of PCT/CN2022/078681, filed Mar. 1, 2022, which claims priority to and benefits of Chinese Patent Application No. 202110455923.6, filed with the China National Intellectual Property Administration on Apr. 26, 2021, the entire contents of both of which are incorporated herein by reference.

TECHNICAL FIELD

The present disclosure relates to a technical field of electronic devices, and more particularly to a wearable device, as well as a heart rate tracking method and a heart rate tracking apparatus thereof.

BACKGROUND

With an increasing living standard, wearable devices are becoming more and more popular. A heart rate tracking algorithm based on a Photo Pethysmo Graphic (PPG) signal is an essential algorithm for wearable devices. The heart rate tracking algorithm generally searches for a current heart rate value near a heart rate at a previous moment, such as +-6BPM (Beat Per Minute). However, after removing interferences, if the quality of the PPG signal is not good, the predicted heart rate value will be brought into a wrong range, which cannot obtain a real heart rate value.

Therefore, it is desirable to improve an accuracy of heart rate tracking of wearable devices.

SUMMARY

Implementations of the present disclosure seek to solve at least one of the problems existing in the related art to at least some extent.

According to implementations of the present disclosure, there is provided a heart rate tracking method for a wearable device, including: obtaining a photo pethysmo graphic (PPG) signal of the wearable device within a preset time window; obtaining a frequency spectrum corresponding to the PPG signal by a short-time Fourier transform of the PPG signal; generating a curve cluster according to the frequency spectrum; and in response to determining a curve that meets a preset condition in the curve cluster, acquiring a jumped heart rate according to the curve that meets the preset condition to track the heart rate.

According to the heart rate tracking method for the wearable device in some implementations of the present disclosure, the PPG signal of the wearable device is obtained within the preset time window, and the frequency spectrum corresponding to the PPG signal is obtained by the short-time Fourier transform of the PPG signal. Then, the curve cluster is generated according to the frequency spectrum, and the curve that meets the preset condition in the curve cluster is determined. When the curve that meets the preset condition exists, the jumped heart rate is acquired according to the curve that meets the preset condition to track the heart rate. In this way, the method provides a mechanism of heart rate jump, which may track a correct heart rate in time, thereby largely improving an accuracy of heart rate prediction.

In some implementations, generating the curve cluster according to the frequency spectrum includes: performing amplitude normalization on the frequency spectrum; obtaining a frequency-amplitude data point by searching for a local peak for the normalized frequency spectrum; in response to determining a current time point greater than zero, pairing a frequency-amplitude data point at the current time point with a frequency-amplitude data point at a previous time point; and generating the curve cluster according to the paired frequency-amplitude data points after pairing is successful.

In some implementations, generating the curve cluster according to the paired frequency-amplitude data points includes: in response to determining the frequency-amplitude data point at the previous time point existing in a first curve, adding the frequency-amplitude data point at the current time point to the first curve; or in response to determining that the frequency-amplitude data point at the previous time point is not in the first curve, generating a second curve according to the frequency-amplitude data point at the previous time point and the frequency-amplitude data point at the current time point; and generating the curve cluster by acquiring the first curve and the second curve within the preset time window.

In some implementations, after obtaining the frequency-amplitude data point of frequency and amplitude by searching for the local peak for the normalized frequency spectrum, the method further includes: in response to determining an amplitude of the frequency-amplitude data point smaller than a preset amplitude, deleting the frequency-amplitude data point whose amplitude is smaller than the preset amplitude.

In some implementations, determining the curve that meets the preset condition in the curve cluster includes: selecting from all curves of the curve cluster a curve where a frequency-amplitude data point at a last time point is consistent with the frequency-amplitude data point at the current time point to generate a curve set; and in response to determining the curve set being not empty, selecting a curve that meets the preset condition from the curve set. The preset condition is that at least one curve in the curve set has a length larger than a preset length, and no other curves exist in a preset frequency range of the at least one curve within a preset period before the current time point.

In some implementations, in response to determining the curve that meets the preset condition in the curve cluster, acquiring the jumped heart rate according to the curve that meets the preset condition to track the heart rate, includes: selecting from the curves that meet the preset condition a curve with a largest length, and determining a frequency at a last time point of the curve with the largest length as the jumped heart rate to track the heart rate.

In some implementations, before obtaining the PPG signal of the wearable device, the method further includes: collecting an optical signal through an optical sensor, in which the optical signal includes the PPG signal and an acceleration signal; and filtering out the acceleration signal from the optical signal by a filtering algorithm to obtain the PPG signal.

According to implementations of the present disclosure, there is provided an apparatus for heart rate tracking, including a processor and a memory for storing instructions executable by the processor. The processor is configured to execute the instructions to perform the above-mentioned heart rate tracking method for the wearable device.

According to the electronic device in some implementations of the present disclosure, the above-mentioned heart rate tracking method for the wearable device is performed based on a mechanism of heart rate jump, which may track a correct heart rate in time, thereby largely improving an accuracy of heart rate prediction.

According to implementations of the present disclosure, there is provided a non-transitory computer-readable storage medium, having stored therein instructions that, when executed by a processor of an electronic device, causes the electronic device to perform the above-mentioned heart rate tracking method for the wearable device.

According to the non-transitory computer-readable storage medium in some implementations of the present disclosure, the above-mentioned heart rate tracking method for the wearable device is performed based on a mechanism of heart rate jump, which may track a correct heart rate in time, thereby largely improving an accuracy of heart rate prediction.

DETAILED DESCRIPTION

Figure 1:
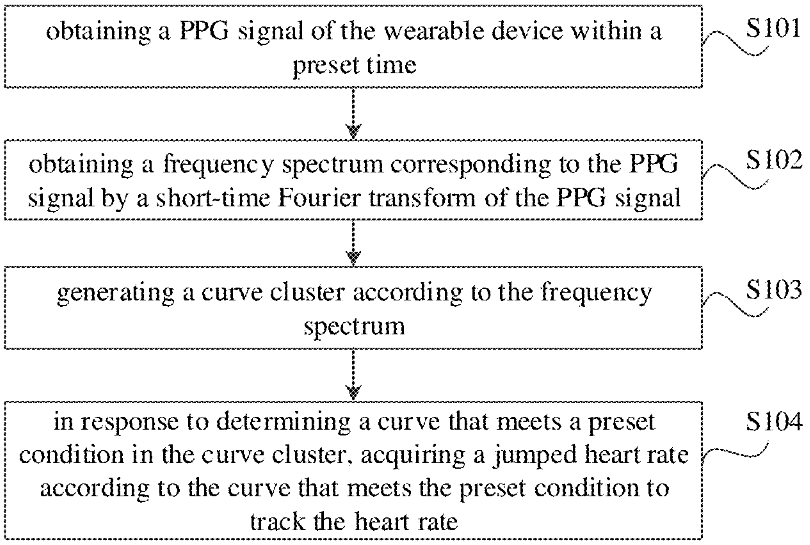
FIG. 1 is a flow chart of a heart rate tracking method for a wearable device in some implementations of the present disclosure.

Implementations of the present disclosure are described in detail below, examples of which are illustrated in the drawings. The same or similar elements are denoted by the same or similar reference numerals in different drawings, unless indicated otherwise. The implementations described herein with reference to drawings are examples, and used to generally understand the present disclosure. The implementations shall not be construed to limit the present disclosure.

A heart rate tracking method for a wearable device, a heart rate tracking apparatus for a wearable device, a wearable device, an electronic device and a non-transitory computer-readable storage medium in some implementations of the present disclosure will be described below with reference to drawings.

FIG. 1 is a flow chart of a heart rate tracking method for a wearable device in some implementations of the present disclosure.

In some implementations of the present disclosure, the wearable device may be, for example, a smart watch or a smart bracelet.

As shown in FIG. 1, the heart rate tracking method for the wearable device in some implementations of the present disclosure includes steps S101 to S104.

In step S101, a photo pethysmo graphic (PPG) signal of the wearable device is obtained within a preset time window.

The preset time window may be set according to actual needs, such as, for example, eight seconds ("8s"). The photo pethysmo graphic is a method where light is irradiated into a skin of a subject (i.e., user) and light scattering caused by blood flow is measured. Specifically, green light emitted by a light emitter such as a light emitting diode (LED) in an optical sensor passes through tissues, arteries and veins in the skin of the subject, and is absorbed or reflected back (i.e., returned) to the optical sensor, which is then detected by a light detector in the optical sensor. The green light reflected back to the optical sensor has a certain attenuation. Unlike blood, the absorption of the green light by muscles, bones, veins and other connecting tissues is basically unchanged (provided that there is no significant movement of measured sites). The blood flows in the arteries, such that the absorption of the green light by the arteries changes. The green light is then transformed into an electronic signal, and the electronic signal may be divided into a direct current (DC) signal and an alternating current (AC) signal due to the changeable absorption of the green light by the arteries and the basically unchangeable absorption of the green light by other tissues. Finally, characteristics of blood flow may be reflected by extracting the AC signal.

In some implementations, before obtaining the PPG signal of the wearable device, the method further includes collecting an optical signal through an optical sensor, in which the optical signal includes the PPG signal and an acceleration signal; and filtering out the acceleration signal from the optical signal by a filtering algorithm to obtain the PPG signal.

In this step, the PPG signal and the acceleration signal may be collected by the optical sensor, such as a PPG optical module. A motion signal, such as the acceleration signal may be filtered out from the PPG signal by the relevant filtering algorithm, such as recursive least squares (PLS), and then the filtered PPG signal is stored for a certain time window, such as, for example, the preset time window of 8s.

In step S102, a frequency spectrum corresponding to the PPG signal is obtained by a short-time Fourier transform of the PPG signal.

In this step, the short-time Fourier transform is performed on a certain amount of the PPG signal to obtain an amplitude value in a certain frequency spectrum interval such as the preset time window, for example, 8s.

In step S103, a curve cluster is generated according to the frequency spectrum.

In some implementations, generating the curve cluster according to the frequency spectrum includes performing amplitude normalization on the frequency spectrum, obtaining a candidate frequency-amplitude data point by searching for a local peak for the normalized frequency spectrum, in response to determining a current time point greater than zero, pairing a frequency-amplitude data point at the current time point with a frequency-amplitude data point at a previous time point, and generating the curve cluster according to the paired frequency-amplitude data points (i.e., the frequency-amplitude data point at the current time point and the frequency-amplitude data point at a previous time point paired to it) after confirming that pairing is successful.

In some implementations, generating the curve cluster according to the paired frequency-amplitude data points includes in response to determining the frequency-amplitude data point at the previous time point existing in a first curve, adding the frequency-amplitude data point at the current time point to the first curve; or in response to determining that the frequency-amplitude data point at the previous time point is not in the first curve, generating a second curve according to the frequency-amplitude data point at the previous time point and the frequency-amplitude data point at the current time point; and generating the curve cluster by acquiring the first curve and the second curve within the preset time window.

In this step, normalization is performed on a maximum value and a minimum value of an amplitude of the frequency spectrum to obtain the normalized amplitude between 0 and 1. For example, normalization may be performed by dividing the amplitude by a maximum amplitude. Then, the frequency-amplitude data point may be obtained by searching for the local peak for the normalized frequency spectrum, such that many frequency-amplitude data points may be obtained.

If the current time point is zero, no processing is performed. If the current time point is greater than zero, a frequency-amplitude data point at the current time point and a frequency-amplitude data point at a previous time point are paired according to a pairing condition. In an implementation, the pairing condition is that the difference between a frequency of the frequency-amplitude data point at the current time point and a frequency of the frequency-amplitude data point at the previous time point is within, for example, 6 BPM. If the frequency-amplitude data point at the current time point and the frequency-amplitude data point at the previous time point meet the pairing condition, it is determined whether the frequency-amplitude data point at the previous time point exists in a first curve. In response to determining the frequency-amplitude data point at the previous time point existing in the first curve, the frequency-amplitude data point at the current time point is added to the first curve. That is to say, a length of the first curve is increased (e.g., by 1 time point or 1s if sampling rate is 1/s). That is, the length is indicative of a number of consecutive time points associated with the at least one curve. In response to determining that the frequency-amplitude data point at the previous time point does not exist in the first curve, a new curve is generated as a second curve according to the frequency-amplitude data point at the previous time point and the frequency-amplitude data point at the current time point. All the generated curves including the first curve and the second curve within the preset time window form the curve cluster.

Figure 2:
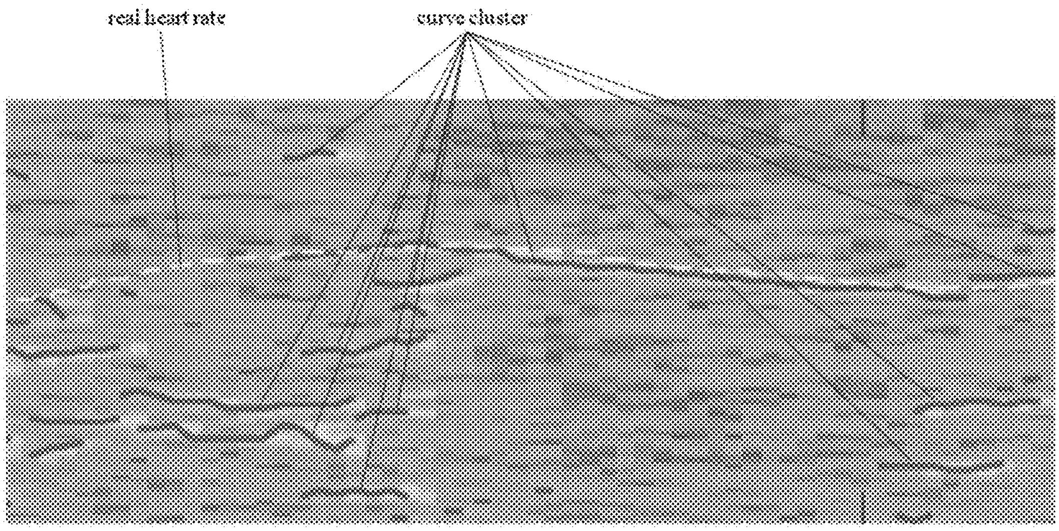
FIG. 2 is a schematic diagram showing a real heart rate and a curve cluster in an implementation of the present disclosure.

With the increase of time, steps S101 to S103 are performed cyclically to obtain continuously growing curve clusters, i.e., continuously update the curve clusters, as shown in FIG. 2. It should be noted that only some of the curves are marked in the curve cluster in FIG. 2, and the curves with the same thickness are also curves in the curve cluster.

In order to further improve the accuracy of heart rate prediction, after obtaining the frequency-amplitude data point by searching for the local peak for the normalized frequency spectrum, the method further includes in response to determining an amplitude of the frequency-amplitude data point smaller than a preset amplitude (i.e., less than a threshold value), deleting the frequency-amplitude data point whose amplitude is smaller than the preset amplitude. The preset amplitude may be set according to actual needs, such as, for example, 0.6.

That is to say, in order to further improve the accuracy of heart rate prediction, after obtaining the frequency-amplitude data point by searching for the local peak for the frequency spectrum, for the normalized amplitude, it can be determined whether an amplitude of the frequency-amplitude data point is smaller than a preset amplitude, and to delete the frequency-amplitude data point whose amplitude is smaller than the preset amplitude, such as, for example, 0.6.

In step S104, in response to determining a curve that meets a preset condition in the curve cluster, a jumped heart rate is acquired according to the curve that meets the preset condition to track the heart rate.

In some implementations, determining the curve that meets the preset condition in the curve cluster includes selecting from all curves of the curve cluster a curve where a frequency-amplitude data point at a last time point is consistent with the frequency-amplitude data point at the current time point to generate a curve set; and in response to determining the curve set being not empty, selecting a curve that meets the preset condition from the curve set. The preset condition is that at least one curve in the curve set has a length larger than a preset length, and no other curves exist in a preset frequency range of the at least one curve within a preset period before the current time point. The preset length, the preset frequency range and the preset time point may be set according to actual needs. For example, the preset length may be 5, the preset frequency range may be in a range of 0 to 0.5 Hz, and the preset period may be a period of 5s (e.g., 5 time points when sampling rate is 1/s) before the current time point.

In some implementations, in response to determining the curve that meets the preset condition in the curve cluster, acquiring the jumped heart rate according to the curve that meets the preset condition to track the heart rate, includes selecting from the curves that meet the preset condition a curve with a largest length, and determining a frequency at a last time point of the curve with the largest length as the jumped heart rate to track the heart rate. The jumped heart rate is therefore indicative of an abrupt change in heart rate for heart rate tracking resulting from the selected curve that meets the preset condition being a standout from the other curves (e.g., having the largest length and no other curves exist in a preset frequency range of the selected curve), as discussed above. In other words, the jumped heart rate is determined as a current heart rate to be jumped to and used as the estimated heart rate for heart rate tracking.

Figure 3:
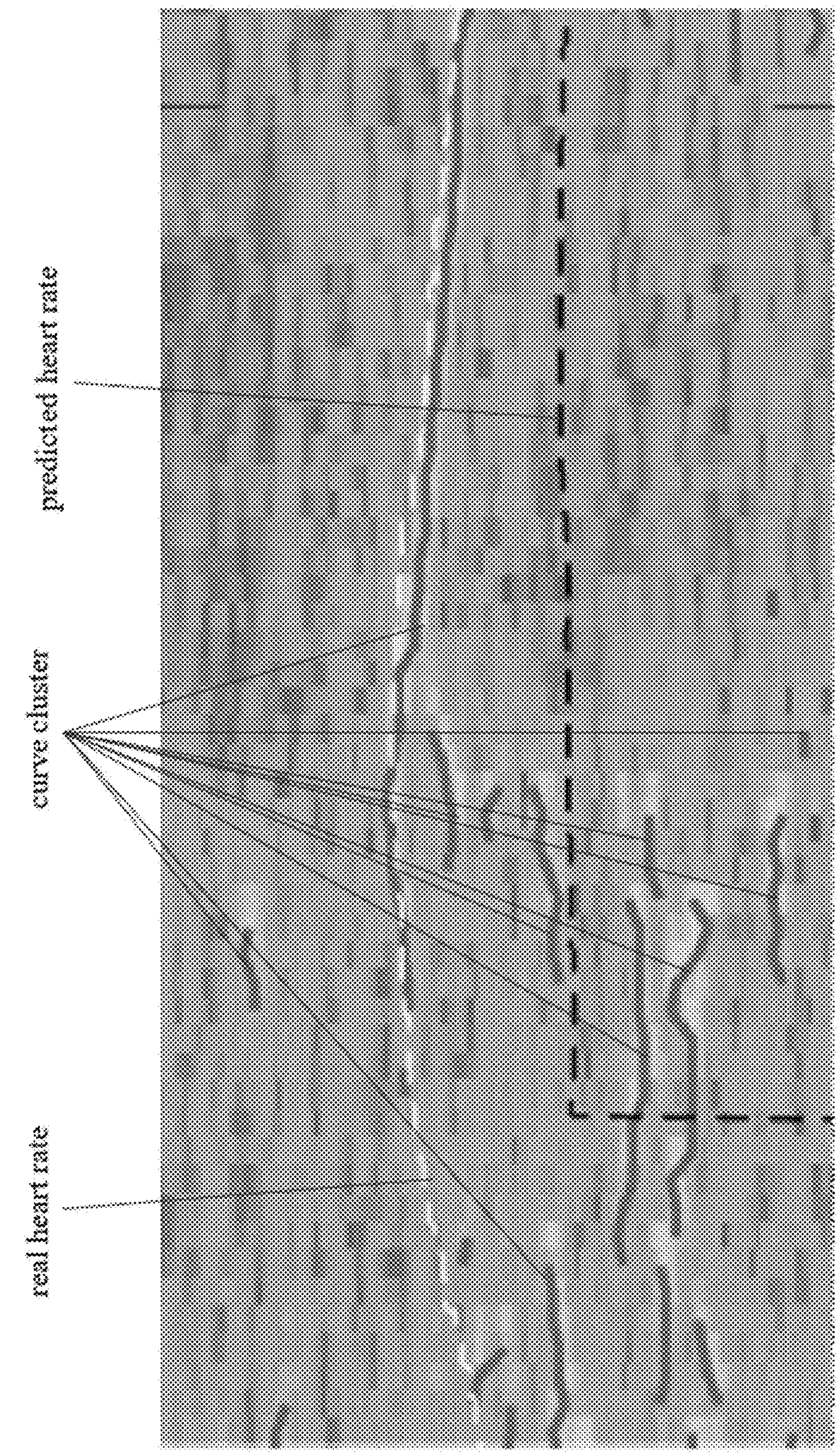
FIG. 3 is a schematic diagram showing a predicted heart rate obtained by a heart rate tracking method for a wearable device in a related art.

According to some existing solutions, a heart rate at a previous time point is first obtained to search for a new heart rate at a current time point within, for example, 6 BPM (beats per minute) of the heart rate at the previous time point. When the heart rate signal is weak, a heart rate tracking error will be amplified, and when the heart rate signal is strong, the algorithm cannot track the heart rate correctly, for example, as shown in FIG. 3.

Figure 4:
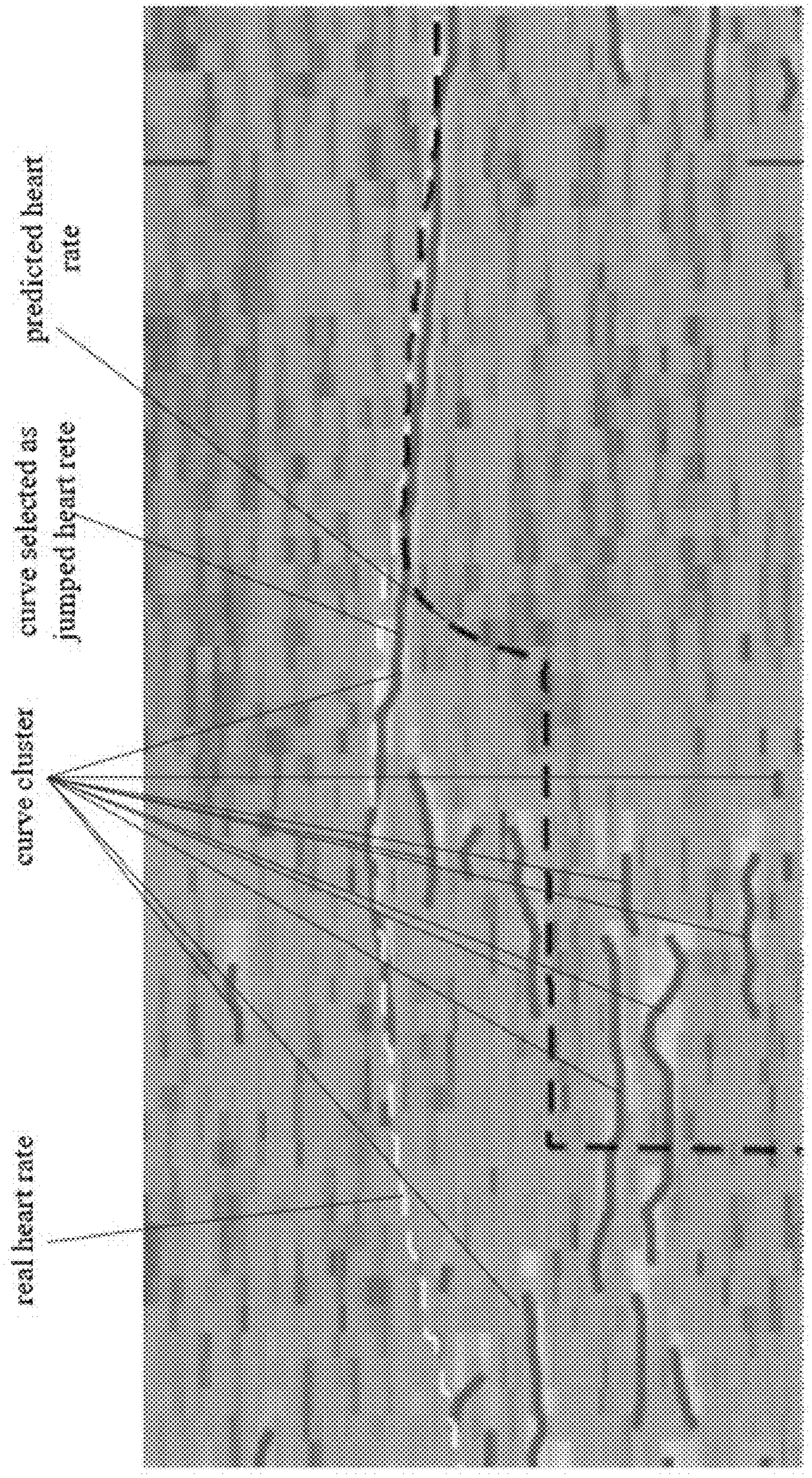
FIG. 4 is a schematic diagram showing a predicted heart rate obtained by a heart rate tracking method for a wearable device in some implementations of the present disclosure.

According to some implementations of this disclosure, after obtaining a curve cluster, a curve where a frequency-amplitude data point at a last time point is consistent with the frequency-amplitude data point at the current time point is selected from all curves of the curve cluster to generate a curve set. Then, it is determined whether the curve set is empty. In response to determining the curve set being not empty, there is a curve L with a length larger than, for example, 5s, and with no other curves existing in, for example, a 0.5 Hz range of the curve L within a period of, for example, 5 time points before the current moment assuming the sampling rate of 1/s. When there is more than one curve L, a curve with a largest length is selected, and a frequency at a last time point of the curve with the largest length is determined as the current heart rate to be jumped to so as to track the heart rate, as shown in FIG. 4.

In this way, the method provides a mechanism of heart rate jump, which may track a correct heart rate in time, thereby largely improving an accuracy of heart rate prediction.

Figure 5:
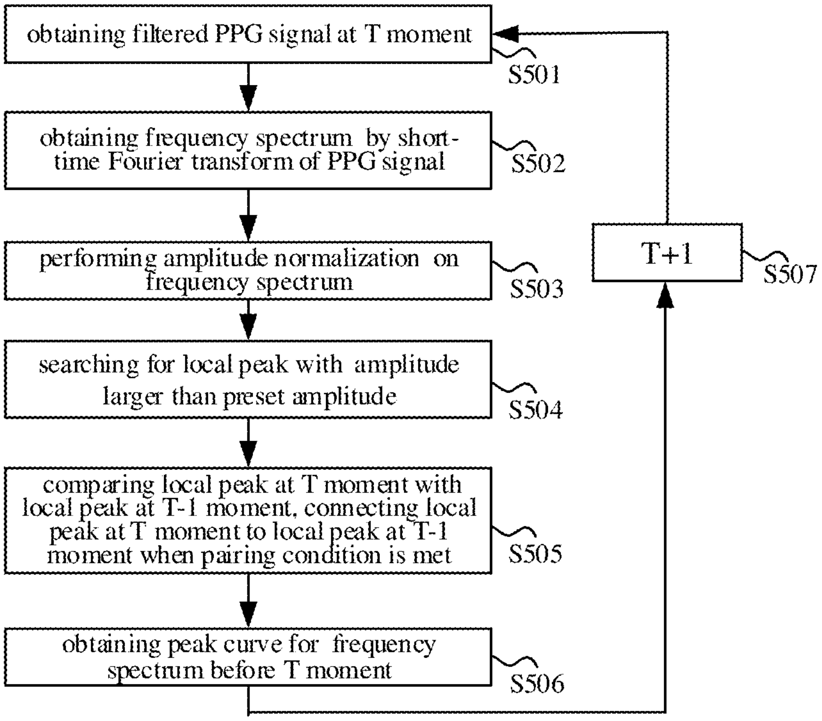
FIG. 5 is a schematic diagram showing a generating process of a curve cluster in a heart rate tracking method for a wearable device in some implementations of the present disclosure.

In order to further illustrate steps S101 to S103, FIG. 5 is a schematic diagram showing a generating process of a curve cluster in a heart rate tracking method for a wearable device according to some implementations of the present disclosure. As shown in FIG. 5, the generating process of the curve cluster in the heart rate tracking method for the wearable device includes steps of S501 to S507.

In step S501, a filtered PPG signal is obtained at time point T.

In step S502, a frequency spectrum corresponding to the PPG signal is obtained by a short-time Fourier transform.

In step S503, amplitude normalization is performed on the frequency spectrum. For example, normalization may be performed by dividing an amplitude by a maximum amplitude to obtain the normalized amplitude between 0 and 1.

In step S504, a local peak with an amplitude larger than a preset amplitude is obtained. The preset amplitude may be, in a non-limiting example, 0.6.

In step S505, a local peak at time point T is compared with a local peak at time point (T-1), and connected to the local peak at time point (T-1) when a pairing condition is met ("matched"). In an implementation, for example, the pairing (i.e., matching) condition is that the difference between a frequency of the frequency-amplitude data point at the current time point and a frequency of the frequency-amplitude data point at the previous time point is within, for example, 6 BPM.

In step S506, a peak curve for the frequency spectrum before time point T is obtained.

In step S507, a filtered PPG signal at time point (T+1) is processed continually.

After obtaining the curve cluster by steps S501 to S507, a curve where a frequency-amplitude data point at a last time point is consistent with the frequency-amplitude data point at the current time point is selected from all curves of the curve cluster to generate a curve set. Then, it is determined whether the curve set is empty. In an example, in response to determining the curve set being not empty, there is a curve L with a length larger than 5s, and with no other curves existing in a 0.5 Hz range of the curve L within a period of 5 time points before the current time point. When there is more than one curve L, a curve with a largest length is selected, and a frequency at a last time point of the curve with the largest length is determined as the current heart rate to be jumped to so as to track the heart rate, as shown in FIG. 4.

According to the heart rate tracking method for the wearable device in some implementations of the present disclosure, the PPG signal of the wearable device is obtained within the preset time window, and the frequency spectrum corresponding to the PPG signal is obtained by the short-time Fourier transform of the PPG signal. Then, the curve cluster is generated according to the frequency spectrum, and the curve that meets a preset condition in the curve cluster is determined. When the curve that meets the preset condition exists, the jumped heart rate is acquired according to the curve that meets the preset condition to track the heart rate. In this way, the method provides a mechanism of heart rate jump, which may track a correct heart rate in time, thereby largely improving an accuracy of heart rate prediction.

Figure 6:
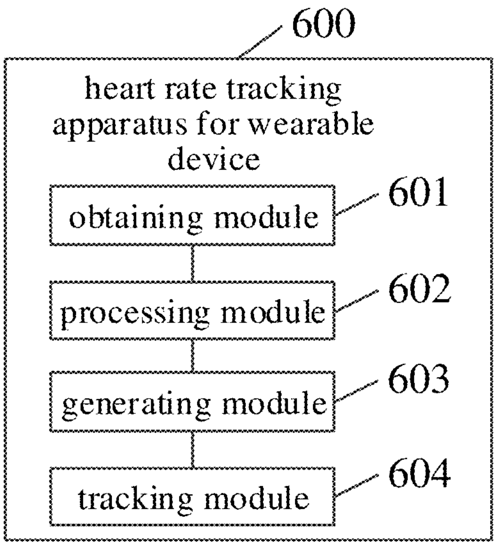
FIG. 6 is a block diagram of a heart rate tracking apparatus for a wearable device in some implementations of the present disclosure.

FIG. 6 is a block diagram of a heart rate tracking apparatus for a wearable device in some implementations of the present disclosure.

As shown in FIG. 6, the heart rate tracking apparatus 600 for the wearable device in some implementations of the present disclosure includes an obtaining module 601, a processing module 602, a generating module 603 and a tracking module 604.

The obtaining module 601 is configured to obtain a PPG signal of the wearable device within a preset time window. The processing module 602 is configured to obtain a frequency spectrum corresponding to the PPG signal by a short-time Fourier transform of the PPG signal. The generating module 603 is configured to generate a curve cluster according to the frequency spectrum. The tracking module 604 is configured to acquire a jumped heart rate according to a curve that meets a preset condition to track the heart rate when it is determined that the curve that meets the preset condition exists in the curve cluster.

In some implementations, the generating module 603 includes a processing unit, a searching unit, a pairing unit and a first generating unit. The processing unit is configured to perform amplitude normalization on the frequency spectrum. The searching unit is configured to obtain a frequency-amplitude data point by searching for a local peak for the normalized frequency spectrum. The pairing unit is configured to pair a frequency-amplitude data point at a current time point with a frequency-amplitude data point at a previous time point when it is determined that the current time point is greater than zero. The first generating unit is configured to generate the curve cluster according to the paired frequency-amplitude data points after pairing is successful.

In some implementations, the first generating unit is configured to in response to determining the frequency-amplitude data point at the previous time point existing in a first curve, add the frequency-amplitude data point at the current time point to the first curve; or in response to determining that the frequency-amplitude data point at the previous time point is not in the first curve, generate a second curve according to the frequency-amplitude data point at the previous time point and the frequency-amplitude data point at the current time point; generate the curve cluster by acquiring the first curve and the second curve within the preset time window.

In some implementations, the generating module 603 further includes a deleting unit. The deleting unit is configured to delete a frequency-amplitude data point whose amplitude is smaller than a preset amplitude when it is determined that an amplitude of the frequency-amplitude data point is smaller than the preset amplitude.

In some implementations, the judging module 604 includes a second generating unit and a selecting unit. The second generating unit is configured to select from all curves of the curve cluster a curve where a frequency-amplitude data point at a last time point is consistent with the frequency-amplitude data point at the current time point to generate a curve set. The selecting unit is configured to select a curve that meets the preset condition from the curve set when it is determined that the curve set is not empty. The preset condition is that at least one curve in the curve set has a length larger than a preset length, and no other curves exist in a preset frequency range of the at least one curve within a preset period before the current time point.

In some implementations, the tracking module 605 is configured to select from the curves that meet the preset condition a curve with a largest length, and determine a frequency at a last time point of the curve with the largest length as the jumped heart rate to track the heart rate.

In some implementations, the heart rate tracking apparatus 600 for the wearable device further includes a collecting module and a filtering module. The collecting module is configured to collect an optical signal through an optical sensor, in which the optical signal includes the PPG signal and an acceleration signal. The filtering module is configured to filter out the acceleration signal from the optical signal by a filtering algorithm to obtain the PPG signal.

It should be noted that, for details not disclosed in the heart rate tracking apparatus for the wearable device in the implementations of the present disclosure, reference is made to the details disclosed in the heart rate tracking method for the wearable device in the implementations of the present disclosure, which will not be described in detail here.

According to the heart rate tracking apparatus for the wearable device in some implementations of the present disclosure, the PPG signal of the wearable device is obtained by the obtaining module within the preset time window, and the frequency spectrum corresponding to the PPG signal is obtained by the processing module through the short-time Fourier transform of the PPG signal. Then, the curve cluster is generated by the generating module according to the frequency spectrum, and the curve that meets a preset condition in the curve cluster is determined by the tracking module. When the curve that meets the preset condition exists, the jumped heart rate is acquired according to the curve that meets the preset condition to track the heart rate. In this way, the apparatus is used based on a mechanism of heart rate jump, which may track a correct heart rate in time, thereby largely improving an accuracy of heart rate prediction.

Figure 7:
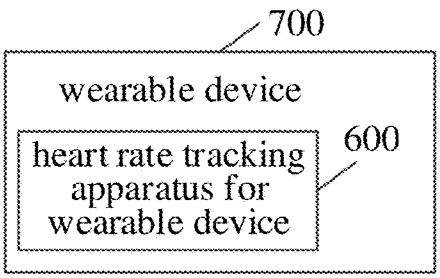
FIG. 7 is a block diagram of a wearable device in some implementations of the present disclosure.

FIG. 7 is a block diagram of a wearable device in some implementations of the present disclosure.

As shown in FIG. 7, the wearable device 700 provided in some implementations of the present disclosure includes the above-mentioned heart rate tracking apparatus 600 for the wearable device.

By the above-mentioned heart rate tracking apparatus for the wearable device, the wearable device provided in some implementations of the present disclosure may be used based on a mechanism of heart rate jump, which may track a correct heart rate in time, thereby largely improving an accuracy of heart rate prediction.

According to the above-mentioned implementations, an electronic device is provided, including a processor and a memory for storing instructions executable by the processor. The processor is configured to execute the instructions to perform the above-mentioned heart rate tracking method for the wearable device.

Figure 8:
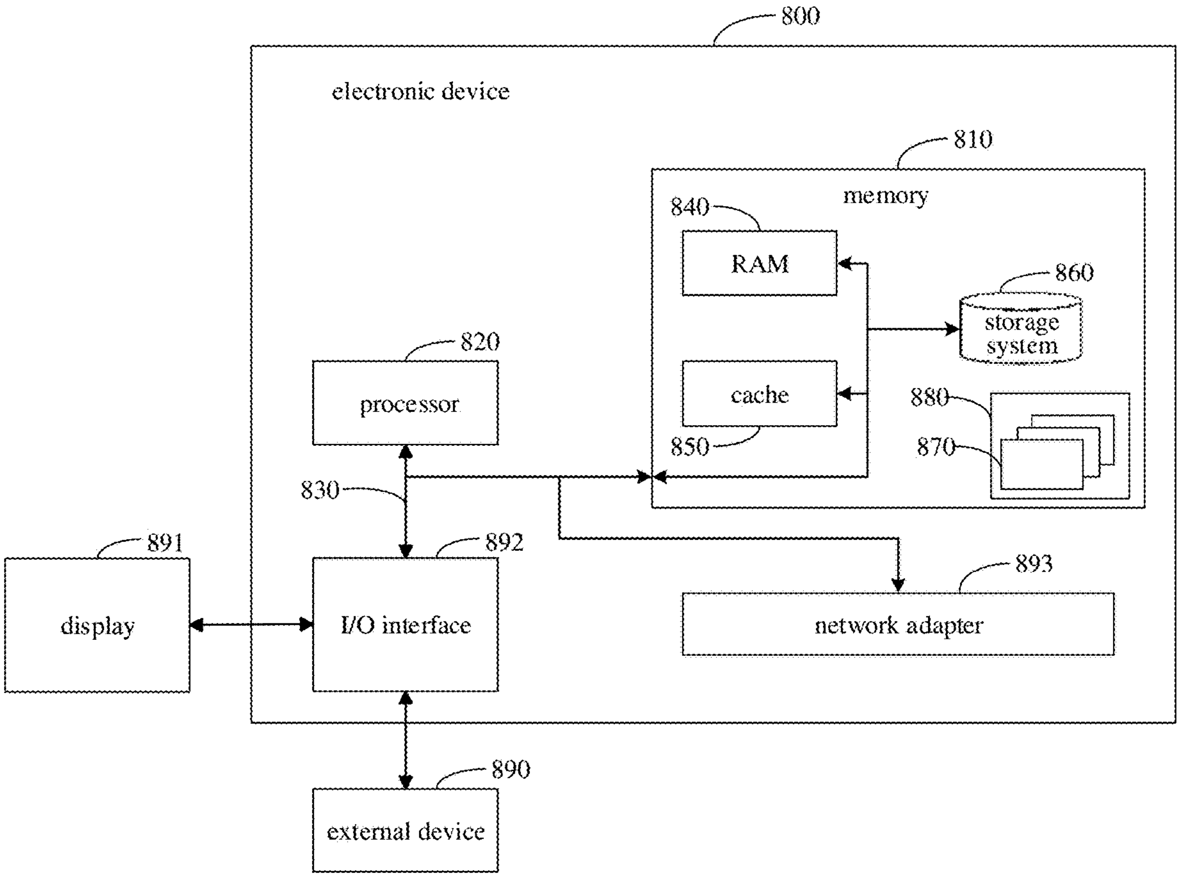
FIG. 8 is a block diagram of an electronic device in some implementations of the present disclosure.

FIG. 8 is a block diagram of an electronic device in some implementations of the present disclosure.

As shown in FIG. 8, the electronic device 800 includes a memory 810, a processor 820 and a bus 830 that couples various components, including the memory 810 and the processor 820.

The memory 810 is configured to store instructions executable by the processor 820. The processor 801 is configured to call and execute the instructions stored in the memory 802 to perform the above-mentioned heart rate tracking method for the wearable device.

The bus 830 represents one or more of any of several types of bus architectures, including a memory bus or a memory controller, a peripheral bus, an accelerated graphics port, and a processor or a local bus using any of a variety of bus architectures. By way of example, such architectures include but are not limited to an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus.

The electronic device 800 typically includes a variety of electronic device readable media. Such media may be any available media that are accessible by the electronic device 800, and include both volatile and non-volatile media, as well as removable and non-removable media.

The memory 810 may include computer system readable media in the form of volatile memory, such as a random access memory (RAM) 840 and/or a cache memory 850. The electronic device 800 may further include other removable/non-removable, volatile/non-volatile computer system storage media. By way of example only, the storage system 860 may be provided for reading from or writing to non-removable, non-volatile magnetic media (not shown in FIG. 8 and typically called a "hard drive"). Although not shown in FIG. 8, a magnetic disk drive for reading from or writing to a removable, non-volatile magnetic disk (e.g., a "floppy disk"), and an optical disk drive for reading from or writing to a removable, non-volatile optical disk such as a CD-ROM, DVD-ROM, or other optical media can be provided. In such instances, each drive can be connected to the bus 830 by one or more data media interfaces. The memory 810 may include at least one program product having a set (e.g., at least one) of program modules that are configured to carry out the functions of implementations of the present disclosure.

For example, a program/utility 880, having a set (at least one) of program modules 870, may be stored in the memory 810. Such program modules 870 include but are not limited to an operating system, one or more functions, other program modules, and program data. Each of the operating system, one or more functions, other program modules, and program data or some combination thereof, may include an implementation of a networking environment. The program modules 870 are generally configured to carry out the functions and/or methods of implementations of the present disclosure as described herein.

The electronic device 800 may also communicate with one or more external devices 890 such as a keyboard, a pointing device, a display 891, etc.; one or more devices that enable a consumer to interact with the electronic device 800; and/or any devices (e.g., network cards, modems, etc.) that enable the electronic device 800 to communicate with one or more other computing devices. Such communication can occur via I/O interfaces 892. In addition, the electronic device 800 can communicate with one or more networks such as a local area network (LAN), a wide area network (WAN), and/or a public network (e.g., the Internet) via a network adapter 893. As depicted, the network adapter 893 communicates with other components of the electronic device 800 via the bus 830. It should be understood that although not shown, other hardware and/or software components could be used in conjunction with the electronic device 800, including, but not limited to: microcodes, device drivers, redundant processing units, external disk drive arrays, RAID systems, tape drives, and data backup storage systems, etc.

The processor 820 is configured to execute the instructions stored in the memory 810 to perform various functions and process data.

It should be noted that concerning an implementation process of the electronic device in some implementations of the present disclosure, reference may be made to the above-mentioned method in the implementations of the present disclosure, which will not be repeated here in detail.

The electronic device provided in some implementations of the present disclosure may be configured to perform the above-mentioned heart rate tracking method for the wearable device based on a mechanism of heart rate jump, which may track a correct heart rate in time, thereby largely improving an accuracy of heart rate prediction.

According to the above-mentioned implementations, a non-transitory computer-readable storage medium is provided, having stored therein instructions that, when executed by a processor of an electronic device, causes the electronic device to perform the above-mentioned heart rate tracking method for the wearable device.

The non-transitory computer-readable storage medium provided in some implementations of the present disclosure may be configured to perform the above-mentioned heart rate tracking method for the wearable device based on a mechanism of heart rate jump, which may track a correct heart rate in time, thereby largely improving an accuracy of heart rate prediction.

According to the above-mentioned implementations, a computer program product is provided, which, when executed by a processor of an electronic device, causes the electronic device to perform the above-mentioned heart rate tracking method for the wearable device.

The computer program product provided in some implementations of the present disclosure may be configured to perform the above-mentioned heart rate tracking method for the wearable device by a mechanism of heart rate jump, which may track a correct heart rate in time, thereby largely improving an accuracy of heart rate prediction.

In the specification, it is to be understood that terms such as “central”, “longitudinal”, “lateral”, “length”, “width”, “thickness”, “upper”, “lower”, “front”, “rear”, “left”, “right”, “vertical”, “horizontal”, “top”, “bottom”, “inner”, “outer”, “clockwise”, “counterclockwise”, “axial”, “radial” and “circumferential” should be construed to refer to the orientation or positional relationship as shown in the drawings. These relative terms are for convenience of description and do not require that the present disclosure be constructed or operated in a particular orientation, which shall not be construed to limit the present disclosure.

In addition, terms such as “first” and “second” are used herein for purposes of description and are not intended to indicate or imply relative importance or significance or to imply the number of indicated technical features. Thus, the feature defined with “first” or “second” may comprise one or more of this feature. In the description of the present disclosure, “a plurality of” means two or more, unless specified otherwise.

In the present disclosure, unless specified or limited otherwise, the terms “mounted,” “connected,” “coupled,” “fixed” and the like are used broadly, and may be, for example, fixed connections, detachable connections, or integral connections; may also be mechanical or electrical connections; may also be direct connections or indirect connections via intervening structures; may also be inner communications or interactions of two elements, which can be understood by those skilled in the art according to specific situations.

In the specification of the present disclosure, unless specified or limited otherwise, a structure in which a first feature is “on” or “below” a second feature may include an implementation in which the first feature is in direct contact with the second feature, and may also include an implementation in which the first feature and the second feature are not in direct contact with each other, but are contacted via an additional feature formed therebetween. Furthermore, a first feature “on,” “above,” or “on top of” a second feature may include an implementation in which the first feature is right or obliquely “on,” “above,” or “on top of” the second feature, or just means that the first feature is at a height higher than that of the second feature; while a first feature “below,” “under,” or “on bottom of” a second feature may include an implementation in which the first feature is right or obliquely “below,” “under,” or “on bottom of” the second feature, or just means that the first feature is at a height lower than that of the second feature.

Reference throughout this specification to “an implementation,” “some implementations,” “an example,” “a specific example,” or “some examples,” means that a particular feature, structure, material, or characteristic described in connection with the implementation or example is included in at least one implementation or example of the present disclosure. Thus, the appearances of the phrases such as “in some implementations,” “in one implementation”, “in an implementation”, “in another example,” “in an example,” “in a specific example,” or “in some examples,” in various places throughout this specification are not necessarily referring to the same implementation or example of the present disclosure. Furthermore, the particular features, structures, materials, or characteristics may be combined in any suitable manner in one or more implementations or examples. In addition, the features described in some implementations or examples may be combined or connected with the features of other implementations or examples by those skilled in the art without contradicting with each other.

Although explanatory implementations have been shown and described, it would be appreciated by those skilled in the art that the above implementations cannot be construed to limit the present disclosure, and changes, alternatives, and modifications can be made in the implementations without departing from the scope of the present disclosure.

What is claimed is:

1. A method of heart rate tracking based on a wearable device comprising an optical sensor, comprising:

collecting, by the optical sensor of the wearable device, a photo pethysmo graphic (PPG) signal associated with a current time point within a preset time window from the optical sensor of the wearable device, wherein the optical sensor comprises a light emitter configured to emit light to a skin of a user associated with the wearable device and a light detector configured to detect light returned from the skin of the user:

receiving, by a processor, the photo pethysmo graphic (PPG) signal associated with the current time point;

determining, by the processor, a frequency spectrum corresponding to the PPG signal associated with the current time point by a short-time Fourier transform of the PPG signal associated with the current time point;

obtaining, by the processor, at least one data point associated with the current time point based on the frequency spectrum associated with the current time point, each of the at least one data point comprising a local peak and a corresponding frequency;

determining, by the processor, at least one curve to which the at least one data point associated with the current time point belongs, wherein a first curve in the at least one curve comprises a first data point associated with the current time point and at least one second data point associated with at least one previous time point within the preset time window, wherein a difference between a corresponding frequency of the first data point and a corresponding frequency of the at least second data point is less than a threshold value; and determining, by the processor, an estimated heart rate of the user for the current time point based on the at least one curve.

2. The method according to claim 1, wherein determining, by the processor, at least one curve to which the at least one data point associated with the current time point belongs, comprises:

matching each of the at least one data point associated with the current time point with at least one data point associated with a previous time point; and in response to determining that the first data point associated with the current time point is matched with the second data point associated with the previous time point, obtaining a curve comprising the first data point and the second data point.

3. The method according to claim 2, wherein obtaining the curve comprising the first data point and the second data point comprises:

in response to determining that the second candidate-data point is associated with an existing curve in a curve cluster associated with the preset time window, adding the first data point to the existing curve; or in response to determining that the second data point is not associated with any curve in the curve cluster associated with the preset time window:

generating, by the processor, a new curve comprising the first data point and the second candidate data point; and adding, by the processor, the new curve to the curve cluster associated with the preset time window.

4. The method according to claim 1, further comprising:

filtering out a data point with a local peak smaller than a preset amplitude from the at least one data point associated with the current time point.

5. The method according to claim 1, wherein determining, by the processor, the estimated heart rate of the user for the current time point based on the at least one curve, comprises:

selecting a curve from the at least one curve, wherein the selected curve has a length larger than a preset length, and the at least one curve does not comprise another curve having a length larger than the preset length in a preset frequency range of the selected curve within a preset period before the current time point, the length of a curve indicative of a number of time points included in the curve; and determining the estimated heart rate of the user for the current time point based on a data point associated with the current time point in the selected curve.

6. The method according to claim 5, wherein determining the estimated heart rate of the user for the current time point based on the data point associated with the current time point in the selected curve comprises:

in response to determining that more than one curve having a length larger than the preset length, selecting a curve with a largest length from the more than one curve as the selected curve; and determining a frequency in the data point associated with the current time point of the selected curve as the estimated heart rate of the user for the current time point.

7. The method according to claim 1, wherein obtaining, by the processor, at least one data point associated with the current time point based on the frequency spectrum associated with the current time point, comprises:

performing amplitude normalization processing on the frequency spectrum associated with the current time point; and obtaining at least one data point by searching for a local peak in the normalized frequency spectrum associated with the current time point.

8. A non-transitory computer-readable storage medium, having stored therein instructions that, when executed by a processor of an electronic device, causes the electronic device to perform the method according to claim 1.

9. The non-transitory computer-readable storage medium according to claim 8, wherein determining, by the processor, at least one curve to which the at least one data point associated with the current time point belongs comprises:

matching each of the at least one data point associated with the current time point with at least one data point associated with a previous time point; and in response to determining that the first data point associated with the current time point is matched with the second data point associated with the previous time point, obtaining a curve comprising the first data point and the second data point.

10. The non-transitory computer-readable storage medium according to claim 9, wherein obtaining the curve comprising the first data point and the second data point comprises:

in response to determining that the second data point is associated with an existing curve in a curve cluster associated with the preset time window, adding the first data point to the existing curve; or in response to determining that the second data point is not associated with any curve in the curve cluster associated with the preset time window:

generating, by the processor, a new curve comprising the first data point and the second data point; and adding, by the processor, the new curve to the curve cluster associated with the preset time window.

11. The non-transitory computer-readable storage medium according to claim 8, wherein determining, by the processor, the estimated heart rate of the user for the current time point based on the at least one curve, comprises:

selecting a curve from the at least one curve, wherein the selected curve has a length larger than a preset length, and the at least one curve does not comprise another curve having a length larger than the preset length in a preset frequency range of the selected curve within a preset period before the current time point, the length of a curve indicative of a number of time points included in the curve; and determining the estimated heart rate of the user for the current time point based on a data point associated with the current time point in the selected curve.

12. An apparatus for heart rate tracking, comprising:

a wearable device comprising an optical sensor wherein the optical sensor comprises a light emitter configured to emit light to a skin of a user associated with the wearable device and a light detector configured to detect light returned from the skin of the user, wherein the optical sensor is configured to collect a photo pethysmo graphic (PPG) signal associated with a current time point within a preset time window from the optical sensor of the wearable device;

a processor;

and a memory for storing instructions executable by the processor;

wherein the processor is configured to execute the instructions stored in the memory to:

obtain, from the photo pethysmo graphic (PPG) signal associated with the current time point determine a frequency spectrum corresponding to the PPG signal associated with the current time point by a short-time Fourier transform of the PPG signal associated with the current time point;

obtain at least one data point associated with the current time point, each of the at least one data point comprising a local peak and a corresponding frequency obtained from the frequency spectrum associated with the current time point;

update a curve cluster associated with the preset time window, the curve cluster comprising a plurality of curves, each of the plurality of curves comprising at least one data point associated with at least one time point within the preset time window; and select a curve from the curve cluster, the selected curve comprising a data point associated with the current time point and having a length larger than a preset length, the length of the selected curve indicative of a number of time points included in the selected curve; and determine an estimated heart rate of the user for the current time point based on the selected curve.

13. The apparatus according to claim 12, wherein the instructions to update the curve cluster associated with the preset time window based on the at least one data point associated with the current time point comprise instructions to:

match each of the at least one data point associated with the current time point with at least one data point associated with a previous time point; and in response to determining that a first data point associated with the current time point is matched with a second data point associated with the previous time point, update the curve cluster to comprise a curve comprising the first data point and the second candidate data point.

14. The apparatus according to claim 13, wherein the instructions to update the curve cluster to comprise the curve comprising the first data point and the second data point comprise instructions to:

in response to determining that the curve cluster comprises a first curve including the second data point, add the first data point to the first curve; or in response to determining that the second data point is not in any curve in the curve cluster:

generate a second curve according to the first data point and the second data point; and add the second curve to the curve cluster.

15. The apparatus according to claim 13, wherein the instructions to match each of the at least one data point associated with the current time point with at least one data point associated with the previous time point further comprise instructions to:

in response to a difference between a frequency of a first data point associated with the current time point and a frequency of a second data point associated with the previous time point, determine that the first data point is matched with the second data point.

16. The apparatus according to claim 12, wherein the instructions executed by the processor further comprise instructions to:

filter out a data point with an amplitude smaller than a preset amplitude from the at least one data point associated with the current time point.

17. The apparatus according to claim 12, wherein the curve cluster does not comprise another curve in a preset frequency range of the selected curve that has a length larger than the preset length.

18. The apparatus according to claim 12, wherein the instructions to determine the estimated heart rate of the user for the current time point based on the selected curve further comprise instructions to:

determine a frequency associated with the current time point of the selected curve as the estimated heart rate of the user for the current time point.

19. The apparatus according to claim 12, wherein the instructions to obtain at least one data point associated with the current time point further comprise instructions to:

perform amplitude normalization processing on the frequency spectrum associated with the current time point; and obtain at least one data point by searching for a local peak in the normalized frequency spectrum associated with the current time point.

20. The apparatus according to claim 12, wherein the apparatus further comprises the optical sensor.

* * * * *